United States Patent [19]

Trojanowski et al.

[11] Patent Number: 5,580,898
[45] Date of Patent: Dec. 3, 1996

[54] METHOD OF STABILIZING MICROTUBULES

[75] Inventors: John Q. Trojanowski; Virginia M-Y. Lee, both of Philadelphia, Pa.

[73] Assignee: The Trustees of the University of Pennsylvania, Philadelphia, Pa.

[21] Appl. No.: 248,234

[22] Filed: May 24, 1994

[51] Int. Cl.$^6$ .................. A61K 31/335; A01N 43/02
[52] U.S. Cl. .................. 514/449; 424/78.08; 424/78.32; 435/240.2; 436/501; 436/548; 436/811; 549/510
[58] Field of Search .................. 435/240.2; 424/78.32, 424/78.08; 514/449; 436/811, 501, 548; 549/510

[56] References Cited

U.S. PATENT DOCUMENTS

| | | | |
|---|---|---|---|
| 5,362,831 | 11/1994 | Mongelli et al. | 526/304 |
| 5,380,751 | 1/1995 | Chen et al. | 514/449 |

OTHER PUBLICATIONS

Everitte–Voegelein et al "J. Nat Prod" vol. 50 No. 1 Jan.–Feb. 1987 Taxol & Derivatives: A Biogenetic Hypothesis pp. 9–18.

Bramblett et al., "Regions with Abundant Neurofibrillary Pathology in Human Brain Exhibit a Selective Reduction in Levels of Binding–Competent τ and Accumulation of Abnormal τ–Isoforms (A68 Proteins)" Lab Invest. 66 212–222, (1992).

Bramblett et al. "The Abnormal Phosphorylation of Tau at Ser$^{396}$ in Alzheimer's Disease Recpaitulates Phosphorylation During Development and Contributes to Reduced Microtubule Binding", Neuron 10: 1089–1099 (1993).

Butner and Kirschner, "Tau Protein Binds to Microtubules Through a Flexible Array of Distributed Weak Sites", *J. Cell Biol* 115: 717–730 (1991).

Drechsel et al., "Modulation of the Dynamic Instability of Tubulin Assembly by the Microtubule–Associated Protein Tau", *Mol. Biol. Cell.* 3: 1141–1154 (1992).

Goedert et al., "Expression of Separate Isoforms of Human Tau Protein: Correlation with the Tau Pattern in Brain and Effects on Tubulin Polymerization", *Embo J.* 9: 4225–4230 (1990).

Kosik et al., "Developmentally Regulated Expression of Specific Tau Sequences", *Neuron* 2: 1389–1387 (1989).

Lee et al., "Tau Proteins are Abnormally Expressed in Olfactory Epithelium of Alzheimer Patients and Developmentally Regulated in Human Fetal Spinal Cord", *Experimental Neurology* 121: 93–105 (1993).

Lindwall et al., "Phosphorylation Affects the Ability of Tau Protein to Promote Microtubule Assembly", *J. Biol. Chem.* 259: 5301–5305 (1984).

Murthy et al., "Microtubule Assembly Using the Microtubule–Associated Protein MAP–2 Prepared in Defined States of Phosphorylation with Protein Kinase and Phosphatase", *Eur. J. Biochem.* 137: 37–46 (1983).

Schiff et al. "Promotion of Microtubule Assembly in Vitro by Taxol", *Nature* 277: 665–667 (1979).

Trojanowski et al., "Altered Tau and Neurofilament Proteins in NeuroDegenerative Diseases: Diagnostic Implications for Alzheimer's Disease and Lewy Body Dementias", *Brain Pathol.* 3:45–54 (1993).

Vallee, "A Taxol–Dependent Procedure for the Isolation of Microtubles and Microtubule–Associated Proteins (MAPs)", *J. Cell Biol.* 92: 435–442 (1982).

Williams and Detrich, "Separation of Tubulin from Microtubule–Associated Proteins on Phosphocellulose. Accompanying Alterations in Concentrations of Buffer Components", *Biochemistry* 18: 2499–2503 (1979).

*Primary Examiner*—Herbert J. Lilling
*Attorney, Agent, or Firm*—Law Offices of Jane Massey Licata

[57] ABSTRACT

A method of stabilizing microtubules which are destabilized due to insufficient levels of normal human tau protein is disclosed. The method comprises the steps of contacting a microtubule that is destablizing due to a deficiency in normal tau protein with an amount of taxol sufficient to stabilize microtubules.

2 Claims, No Drawings

METHOD OF STABILIZING MICROTUBULES

FIELD OF THE INVENTION

The present invention relates to methods of stabilizing microtubules which are unstable microtubules due to the absence of normal tau protein and the presence of A68 protein.

BACKGROUND OF THE INVENTION

Alzheimer disease. (AD) is a disorder of the later decades of life characterized by dementia. In clinical terms, it consists of a diffuse deterioration of mental function, primarily in thought and memory and secondarily in feeling and conduct. AD has also been used to designate dementia appearing before the age of 65 years.

The true incidence of the disorder is unknown, although recent data suggest that the incidence of all dementia in the U.S. population may be over 100 cases per 100,000, with its prevalence being over 550 per 100,000. AD probably affects at least 30 to 50% of patients with dementia, and in the United States there may be over one million individuals with severe dementia and several million more with mild to moderate dementia. It has been estimate that 1 out of every 6 persons over the age of 65 in the United States suffers from moderate dementia, and a majority of patients in nursing home populations are affected with the disorder. The average age of onset is between 70 and 79 years, but without better information on the population at risk, a more accurate statement is not presently possible. The incidence of the syndrome clearly increases with advancing age. A family history of AD is present in 5 to 10% of the patients.

The major abnormalities observed in individuals suffering from AD include the deposition of β-amyloid peptides (Aβ) in the extra-cellular space, the massive loss of cortical neurons and the accumulation of paired helical filaments (PHFs) in the neurofibrillary tangles (NFTs), dystrophic neurites and neuropil threads (NTs). The subunit proteins of PHFs are derivatized forms of CNS τ proteins known as, interchangeably, A68 or PHF τ. Relative to adult CNS τ proteins, PHS τ is excessively phosphorylated and far more resistant to proteolysis than its normal counterpart, but fetal CNS τ is phosphorylated at similar sites.

Despite intense research into the pathological significance of Aβ deposits for over a decade, the role of Aβ in the pathogenesis of AD remains enigmatic. Indeed, abundant deposits of Aβ occur in the brains of elderly individuals who show no antemortem evidence of dementia. On the other hand, the presence of mutations in the APPs within or flanking the Aβ domain in a subset of familial AD kindred provide circumstantial evidence for the involvement of Aβ and APPs in the etiology of some forms of AD.

In contrast, considerable information is available on the basic biology, pathology and normal functions of adult and fetal CNS τ proteins. CNS τ proteins are a group of developmentally regulated low molecular weight microtubule-associated proteins that bind to MTs. They function to stabilize MTs in the polymerized state and facilitate the polymerization of tubulin into MTs. Normal adult human brain τ consists of six alternatively spliced proteins encoded by the same gene, and each τ isoform contains either 3 or 4 consecutive MT binding motifs. Further, human τ isoforms differ with respect to the presence or absence of inserted sequences in the amino-terminal third of τ that are 29 or 58 amino acids in length. So-called "fetal" τ is the shortest τ isoform, and it is expressed early in the developing human nervous system, while all 6 alternatively spliced τ isoforms (including "fetal" CNS τ) are expressed in the adult human brain.

There is a need for a method of stabilizing microtubules in the presence of A68 protein which are undergoing microtubule destabilization due to a deficiency in normal CNS tau protein that stabilizes microtubule polymerization. There is a need for a method of stabilizing microtubules in the presence of A68 protein in cells undergoing microtubule destabilization due to a deficiency in normal CNS tau protein that stabilizes microtubule polymerization.

SUMMARY OF THE INVENTION

The present invention relates to a method of stabilizing microtubules which are unstable due to the presence of A68 protein and the absence of normal tau protein. The method of the present invention comprises the step of contacting microtubules with taxol; the microtubules being in contact with insufficient normal tau protein to stabilize microtubule polymerization.

The present invention relates to a method of stabilizing microtubules in a cell with unstable microtubules. The method of the present invention comprises the step of contacting a cell that is experiencing microtubule destabilization due to a deficiency in normal tau protein that stabilizes microtubule polymerization with an amount of taxol effective to stabilize microtubules. The cell experiencing microtubule destabilization due to a deficiency in normal tau protein is characterized by an accumulation of A68 protein.

DETAILED DESCRIPTION OF THE INVENTION

As used herein, the term "stabilizing microtubules" is meant to refer to the process of maintaining tubulin subunits in a polymerized state in order to produce and maintain microtubules as polymers.

As used herein, the term "unstable microtubules" is meant to refer to depolymerized and/or unpolymerized tubulin subunits.

As used herein, the term "experiencing microtubule destabilization" is meant to refer to the process whereby conditions bring about a depolymerization of microtubules and the tubulin subunits remain unpolymerized.

As used herein, the term "deficiency in normal tau" refers to the absence of normal tau at levels sufficient to maintain the stability of microtubules wherein destabilization of microtubules results.

The deposition of Aβ peptides in diffuse and neuritic amyloid plaques as well as the accumulations of NFTs are not restricted to AD, and deposits of Aβ may be as profuse in cognitively intact elderly individuals as they are in AD patients. However, there is a close correlations between the burden of NFTs and the dementia in AD. Further, τ proteins are the building blocks of NFTs and related neurofibrillary lesions. PHFs are found in NFTs in the perikarya of selectively vulnerable populations of neurons in AD. Despite similarities between the amyloid fibrils and PHFs, amyloid fibrils and PHFs are composed of different proteins. Specifically, amyloid fibrils are formed from 39–43 amino acid long Aβ peptides that are normal cleavage products of the APPs while PHFs are composed of derivatized forms of each of the normal adult CNS τ proteins referred to here as PHF τ.

PHFs are the major structural elements of NFTs, but PHFs also accumulate in dystrophic processes known as NTs when they are dispersed throughout the CNS gray matter. Similar dystrophic neurites also are intermingled with Aβ fibrils in neuritic and diffuse amyloid plaques as well as in the olfactory epithelium. Controversy about the identity of the subunit proteins of PHFs persisted until sodium dodecyl sulfate soluble PHFs were purified from AD brains and shown to consist of CNS τ proteins abnormally phosphorylated at specific residues (e.g. at $Ser^{396}$). Furthermore, AD PHFs were shown to contain all 6 alternatively spliced human CNS τ proteins. Subsequent studies showed that recombinant human τ polymerizes into PHF-like structures under in vitro conditions.

To understand the mechanisms whereby normal adult CNS τ is converted into PHF τ in AD, a number of laboratories sought to identify the sites of aberrant phosphorylation that distinguish PHF τ from normal adult CNS τ. For example, two Ser residues found in all CNS τ isoforms that are abnormally phosphorylated in PHF τ relative to adult human CNS τ were identified (i.e. $Ser^{202}$ and $Ser^{396}$) using immunological methods, synthetic τ phospho-peptides and recombinant human τ subjected to site-directed mutagenesis and in vitro phosphorylation. Further, mass spectrometry and protein/peptide sequencing studies showed that in additional to $Ser^{202}$, $Ser^{396}$ and $Ser^{404}$, PHF τ also is abnormally phosphorylated at $Thr^{181}$, $Thr^{231}$, $Ser^{235}$ and $Ser^{262}$ relative to adult postmortem brain derived CNS τ. These studies indicate that all of the major sites of abnormal phosphorylation in PHF τ are Ser/Pro or Thr/Pro sites.

$Ser^{396}$ and $Ser^{404}$ are both nearby to the MT binding domain just carboxy terminal to the last MT binding repeat. Furthermore, an inverse relationship has been observed between the extent to which τ is phosphorylated and the ability of τ to bind MTs. The aberrant phosphorylation of $Ser^{396}$ in PHF τ relative to normal adult human CNS τ is believed to be involved in the loss of the ability to PHF τ to bind to MTs. When the phosphorylation state of PHF τ was compared with adult and fetal CNS τ proteins, the phosphorylation state of PHF τ partially recapitulates the phosphorylation state of fetal CNS τ. Despite the fact that fetal human CNS τ is phosphorylated at $Ser^{202}$ and $Ser^{396}$ like PHF τ, fetal human τ is capable of binding to MTs, while PHF τ completely loses the ability to bind MTs. However, this loss of function is reversible since dephosphorylation of PHF τ restores the ability to PHF τ to bind MTs.

Although current understanding of the detailed pathobiology of AD and the significance of neurofibrillary lesions in this disease are incomplete at this time, the available information suggests that the conversion of normal τ into PHF τ might have deleterious effects on neurons during the progression of AD. For example, it is well known that the accumulation of PHF τ in AD cortex correlates with the abundance of NFTs as well as with diminished levels of normal MT binding competent τ in the CNS. Further, since abnormal or excessively phosphorylated PHF τ is unable to bind to MTs, we have proposed that the conversion of normal τ into PHF τ could lower the levels of MT binding τ, destabilize MTs, disrupt axonal transport, and lead to the "dying back" of axons in AD. Additionally, disruption of the MT network in neurons could alter the targeting and translation of mRNA in different neuronal domains.

The abnormally phosphorylated CNS τ present in PHFs disrupts the microtubule (MT) network, impair axonal transport and compromise the function and viability of neurons. Since this contributes to the development and progression of AD, MT stabilizing drugs can be used to impede the disruption of microtubules.

According to the present invention, a cell that has a deficiency in normal tau and that is therefore experiencing microtubule destabilization is contacted with taxol or an analog thereof in order to maintain microtubule stability. Applicants have discovered that abnormally phosphorylated tau, A68, is produced in some cells in place of normal tau. The A68 protein lacks the ability to stabilize microtubules which is an activity that normal tau performs. Thus, in such cells, the loss of production of normal tau in favor of production of A68 results in destabilized microtubules and eventual loss of cellular integrity and eventual degeneration of the cell. By contacting the cell with taxol or an analog thereof, the destabilization of the microtubules is prevented. The taxol or analog thereof stabilizes the microtubules in place of the normal tau. The cellular cytoskeleton is maintained and the cell remains intact and functioning.

A class of MT stabilizing drugs (e.g. Taxol, Taxotere and related analogs) that have been used for some time as cancer drugs because of their anti-mitotic effects may be the most promising near term candidates for investigation as therapeutic agents for the treatment of AD. These speculations are consistent with current views of the regulation of tubulin assembly, the functions of MTs, and the role of τ proteins in promoting the assembly and stability of MTs.

Taxol can be extracted from the bark of the Pacific yew tree and is described in Schiff, P. B. et al. (1979) Nature 277:665–667, which is incorporated herein by reference. Taxol may be obtained from Hauser Chemical Co. Bristol-Meyers Squibb Company is currently developing taxol as a pharmaceutical composition for treating ovarian cancer. One having ordinary skill in the art can obtain taxol form commercially available sources or isolate the compound using well known techniques.

It is contemplated that taxol analogs may be used in place of taxol. Examples of taxol analogs include the compound taxotere. One having ordinary skill in the art can test taxol analogs for activity according to the present invention using the microtubule binding assay described herein.

The progressive disruption of several different components of the neuronal cytoskeleton is a common feature of chronic dementias of the elderly, and alterations of the phosphorylation state and degradation of CNS τ in AD is one of the most extensively studies examples of this kind of pathological process. While the disruption of the neuronal cytoskeleton and the incorporation of abnormally phosphorylated CNS τ proteins into pathological inclusions provide markers for AD, these events also could compromise the function and viability of neurons thereby contributing to the emergence of dementia in AD.

To study the efficacy of treating cells with taxol when normal tau levels are inadequate to stabilize MTs, water soluble A68, human adult tau and human fetal tau were purified as follows. Crude A68 preparations obtained from the cerebral cortex of AD patients were fractionated on a sucrose gradient. Enriched A68 from the 1.25M to 1.5M and the 1.75M to 2.0M sucrose layers was solubilized in 2M guanidine isothiocyanate, incubated at 37° C. for 60 minutes, centrifuged for 30 minutes at 100,000×g and dialyzed exhaustively against distilled water. After centrifugation, the dilute A68 in the supernatant was lyophilized and resuspended in re-assembly (RA) buffer (0.1M MES, 0.5 mM $MgSO_4$, 1 mM EGTA, 2 mM DTT pH 6.8) at 1 mg/ml for MT binding assay. Human adult tau was isolated from normal brain by well known techniques. Briefly, high salt extracted, heat and acid stable adult tau was further purified by cycling with exogenous phosphocellulose purified bovine tubulin in the presence of taxol. Human fetal tau was prepared in a similar manner except that the final purification step (i.e. cycling with MTs) was omitted.

Dephosphorylated A68 and tau samples were prepared as follows. Dephosphorylation of A68, human adult and fetal tau, and enriched tau preparations obtained from CHO cells transfected with various tau constructs were carried out overnight at 37° C. using 10 U/ml type III-N *E. coli* alkaline phosphatase (Sigma Fine Chemicals) in RA buffer containing protease inhibitors but without phosphatase inhibitors. Control samples were incubated identically, except that alkaline phosphatase was omitted from the samples.

A microtubule binding assay was performed as follows. Twice cycled bovine MTs were prepared and subjected to phosphocellulose chromatography to isolate pure tubulin. The tubulin was then assembled into MTs by warming to 37° C. for 20 minutes in RA buffer containing 2 mM GTP and 20 μM taxol (RAGT buffer) to stimulate polymerization. Pre-assembled MTs were then added to solutions of native or dephosphorylated A68 or adult tau to yield 1 mg/ml of tubulin and 0.1 mg/ml of tau. After incubation at 37° C. for 20 minutes, the MT binding fraction was separated from the non-binding fraction by centrifugation at 50,000×g for 30 minutes, leaving the non-binding fraction in the supernatant. The MT pellets were resuspended in 100 μl of RAGT buffer and centrifuged through a 100 μl cushion of 10% sucrose in RAGT buffer to remove non-specifically bound protein. The first and second supernatant fractions were combined as the MT non-binding fraction of tau. The MT binding fraction was separated from the MTs by a wash in 0.75M NaCl in RAGT buffer.

The MT binding assay was also conducted using CHO cells transfected with human tau isoforms $Ser^{396}$ 4R and mutant $Ala^{396}$ 4R. Briefly, $1-2 \times 10^6$ transfected CHO cells were incubated for 20 minutes at 37° C. with 0.5% Triton X-100 in 4M glycerol or 20 μM taxol in RA buffer containing 2 mM GTP and a cocktail of protease and phosphatase inhibitors (2 mM PMSF, 20 mM NaF, 0.5 mM Na orthovanadate and 1 μg/ml each of TPCK, TLCK, leupeptin, pepstatin and soy bean trysin inhibitor), followed by centrifugation through a 100 μl sucrose cushion to obtain MT-binding competent and incompetent fractions.

It has been observed that in the presence of taxol, the absence of normal human tau does not result in the destabilization of MTs while in the in the absence of taxol and normal human tau, the MTs destabilize. In some preferred embodiments, the MTs are in cells. In some preferred embodiments, taxol is contacted with MTs at a concentration of 0.1 mM to 1M. In some preferred embodiments, taxol is contacted with MTs at a concentration of 1 mM to 0.1M. In some preferred embodiments, taxol is contacted with MTs at a concentration of 10 mM to 0.01M. In some preferred embodiments, taxol is contacted with MTs at a concentration of 20 mM.

Individuals who are suspected of suffering from AD may be treated by administering to such individuals, an amount of taxol effective to stabilize MTs in the brain cells of such individuals which are deficient in normal tau and which are characterized by the presence of A68.

Pharmaceutical compositions which comprise taxol can be used to stabilize MTs in cells where the normally MT-stabilizing normal tau protein is deficient.

Diagnosis of individuals suspected of suffering from AD may be readily made by those having ordinary skill in the art.

Taxol can be formulated for prophylactic and therapeutic applications by those having ordinary skill in the art.

The range of amounts of a compound to be administered to an individual to be effective in treating or preventing AD by stabilizing MTs in cells deficient in normal tau can be determined by those having ordinary skill in the art.

Cells in individuals suffering from AD include those characterized by the presence of A68. In addition, taxol may be administered to individuals suffering from other diseases and conditions characterized by the presence of A68 instead of the normal tau protein.

Pharmaceutical compositions that comprise taxol may be administered by any method that can deliver the compound to the brain. Methods of pharmaceutical administration include but are not limited to oral, subcutaneously, transdermal, intravenous, intramuscular and parenteral methods of administration. Taxol may implanted as a time release composition directly into the brain tissue of an individual. Pharmaceutical compositions that comprise taxol or an analog thereof are administered to individuals in therapeutically effective amounts. The dosage administered in any particular instance will depend upon factors such as the mode and route of administration; age, health, and weight of the recipient; nature and extent of symptoms; kind of concurrent treatment, frequency of treatment, and the effect desired. The range of the amount of taxol or an analog thereof that is effective for stabilizing MTs in the brain cells of individuals suffering from AD can be determined by one having ordinary skill in the art. It is contemplated that the daily dosage of taxol or an analog thereof of the invention will be in the range of from about 0.001 mg to about 10 mg per kg of body weight, preferably from about 0.01 mg to about 1 mg per kg body weight. It is also contemplated that the daily dosage of taxol or an analog thereof of the invention may be in the range of from about 0.25–0.50 mg to about 20 mg per kg of body weight. Pharmaceutical compositions of the invention may be administered in a single dosage, divided dosages or in sustained release. Persons of ordinary skill will be able to determine dosage forms and amounts with only routine experimentation based upon the considerations of this invention. Taxol may be formulated into dosage forms according to standard practices in the field of pharmaceutical preparations. See *Remington's Pharmaceutical Sciences*, A. Osol, Mack Publishing Company, Easton, Pa.

We claim:

1. A method of stabilizing microtubules in individuals suspected of suffering from Alzheimer's disease comprising the step of:

(a) contacting a microtubule experiencing destabilization due to a deficiency in normal tau protein with an amount of taxol sufficient to stabilize microtubules.

2. The method of claim 1 wherein said microtubules are with a cell.

* * * * *